United States Patent [19]

Giroux

[11] 4,097,371

[45] Jun. 27, 1978

[54] SEPARATION OF FLUID MIXTURES

[75] Inventor: Victor A. Giroux, Bartlesville, Okla.

[73] Assignee: Phillips Petroleum Company, Bartlesville, Okla.

[21] Appl. No.: 725,306

[22] Filed: Sep. 21, 1976

[51] Int. Cl.² .......................... B01D 3/40; C10G 7/00
[52] U.S. Cl. .................................. 208/313; 203/81; 260/674 SE
[58] Field of Search ................ 208/313; 260/674 SE; 203/81

[56] References Cited

U.S. PATENT DOCUMENTS

| | | | |
|---|---|---|---|
| 2,961,383 | 11/1960 | Black | 208/313 |
| 3,037,062 | 7/1962 | Gerhold | 260/674 SE |
| 3,059,037 | 10/1962 | Cahn | 260/674 SE |
| 3,763,037 | 10/1973 | Thompson | 208/313 |

Primary Examiner—Herbert Levine

[57] ABSTRACT

A fluid mixture, such as pyrolysis gasoline, is fractionated into at least two aromatic-rich streams. These streams are introduced into an extractive distillation column at different elevations, with the stream containing the highest boiling aromatic being introduced at the highest elevation.

9 Claims, 2 Drawing Figures

SEPARATION OF FLUID MIXTURES

It is often desirable to separate aromatics from fluid mixtures which also contain paraffins and naphthenes. For example, it is common practice to produce ethylene, propylene and other light hydrocarbons by thermal cracking of naphtha feed streams. Such a cracking operation produces an effluent stream which contains substantial quantities of aromatics. After fractionation to recover the light hydrocarbons, an aromatic-rich stream remains which is often referred to as pyrolysis gasoline. It is desirable to recover benzene, toluene and xylenes present in this pyrolysis gasoline. While separations of this type can be performed in extractive distillation columns, it is difficult to produce product streams of high purity because of the presence of a variety of paraffins and naphthenes which have boiling points in the range which encompasses the boiling point range of the aromatics. It is also desirable to recover the paraffins and naphthenes because these hydrocarbons can be reformed to produce more aromatics.

In accordance with one embodiment of this invention, an improved process is provided for recovering aromatics from a fluid mixture, such as a pyrolysis gasoline, which also contain paraffins and naphthenes. The mixture is first fractionated to obtain at least two product streams. In one mode of operation, the first stream is rich in benzene and the second stream is rich in toluene and xylenes in one embodiment. In another mode of operation, the fluid mixture is fractionated into three streams which are rich in benzene, toluene and xylenes, respectively. The resulting streams are introduced into an extractive distillation column at separate locations. In both modes, the benzene stream is introduced at a lower elevation, with the other stream or streams introduced at higher elevations. When three streams are separated, the xylene-rich stream is introduced at the uppermost location. A solvent which is selective for the aromatics, such as sulfolane, is introduced into the upper region of the extractive distillation column. This produces an extract stream which contains the aromatics and a raffinate stream which contains paraffins and naphthenes. The aromatics can be recovered separately from the extract stream.

In the accompanying drawing.

Figure 1:
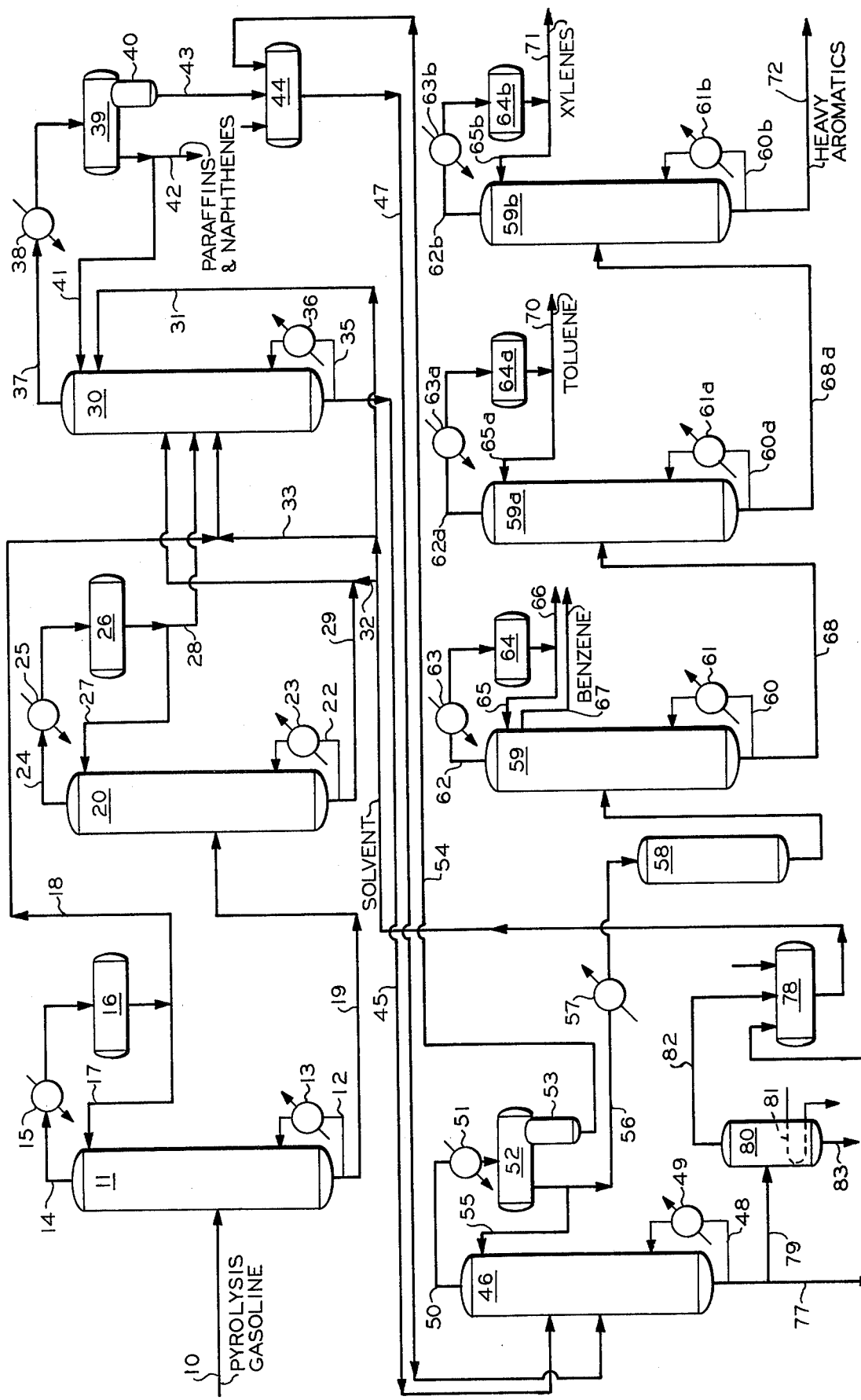
FIG. 1 is a schematic representation of apparatus which can be employed to carry out one method of this invention.

Referring now to the drawing in detail and to FIG. 1 in particular, a stream of pyrolysis gasoline is introduced through a conduit 10 which communicates with a fractionation column 11. Heat is supplied to the lower region of the column by directing liquid from the bottom of the column through a conduit 12 which has a reboiler 13 associated therewith. Vapors removed from the top of column 11 are directed through a conduit 14 to a condenser 15, with the resulting condensate being delivered to an accumulator 16. A portion of the condensate is returned to column 11 as reflux through a conduit 17. The remainder is removed through a conduit 18.

A liquid product stream is removed from the bottom of column 11 through a conduit 19 which communicates with a second fractionation column 20. Heat is supplied to the lower region of column 20 by passing liquid from the bottom of the column through a conduit 22 which has a reboiler 23 associated therewith. Vapors are removed from the top of column 20 through a conduit 24 which communicates with a condenser 25. The resulting condensate is delivered to an accumulator 26. A portion of this condensate is returned to column 20 as reflux through a conduit 27. The remainder of the condensate is removed through a conduit 28. A liquid kettle product is removed from the bottom of column 20 through a conduit 29.

As will be discussed hereinafter in greater detail, columns 11 and 20 are operated so that the stream removed through conduit 18 is rich in benzene. The stream removed through conduit 28 is rich in toluene, and the stream removed through conduit 29 is rich in xylenes. The paraffins and naphthenes present in the pyrolysis gasoline feed stream are fractionated in accordance with their respective boiling points so that these constituents appear in part in each of the conduits 18, 28 and 29.

Conduits 18, 29 and 28 communicate with an extractive distillation column 30 at locations spaced from one another. As illustrated, the benzene-rich stream is introduced at the lower level, the toluene-rich stream is introduced at an intermediate level, and the xylenes-rich stream is introduced at an upper level. A stream of a solvent which selectively absorbs the aromatics in preference to the paraffins and naphthenes is introduced into the upper region of column 30 through a conduit 31. Additional solvent can be introduced through conduits 32 and 33 which communicate with respective conduits 29 and 18. The solvent can be any material which selectively absorbs the aromatics. Examples of suitable solvents include sulfolane, diethylene glycol, triethylene glycol and dimethylformamide, for example. A small amount of water, 0.5 to 2.5 weight percent for example, is often added to the organic solvent. Heat is supplied to the lower region of column 30 by passing a portion of the liquid in the bottom of the column through a conduit 35 which has a reboiler 36 associated therewith. Vapors are removed from the top of column 30 through a conduit 37 which communicates with a condenser 38. The resulting condensate is delivered to an accumulator 39 which has a settling leg 40 therein. The solvent can include an aqueous material, as discussed above, which settles in leg 40. A portion of the hydrocarbon phase in accumulator 39 is returned to column 30 as reflux through a conduit 41. The remainder of this liquid, which comprises paraffins and naphthenes, is removed through a conduit 42. The aqueous solvent phase is passed through a conduit 43 to a storage vessel 44. Additional water can be added to vessel 44 as needed.

The extract stream removed from extractive distillation column 30 is passed by a conduit 45 to an intermediate region of a stripping column 46. The aqueous phase of the solvent is passed from vessel 44 through a conduit 47 to the lower region of stripping column 46. Heat is supplied to the lower region of column 46 by passing a portion of the liquid in the lower region thereof through a conduit 48 which has a reboiler 49 associated therewith. Vapors are removed from the top of column 46 through a conduit 50 which communicates with a condenser 51. The resulting condensate is delivered to an accumulator 52 which is provided with a settling leg 53. The aqueous phase is removed from settling leg 53 and passed through a conduit 54 to storage vessel 44. A portion of the organic phase in accumulator 52 is returned to column 46 as reflux through a conduit 55. The remainder of this liquid, which comprises the aromatics to be recovered, is removed through a conduit 56.

The aromatic stream removed from accumulator 52 is passed by conduit 56 through a heater 57 and a treater 58 to the inlet of a fractionation column 59. Treater 58 can comprise a tower filled with clay to remove odor and color forming impurities. Heat is supplied to the lower region of column 59 by passing liquid from the bottom thereof through a conduit 60 which has a reboiler 61 associated therewith. Vapors removed from the top of column 59 are passed by a conduit 62 to a condenser 63. The resulting condensate is delivered to an accumulator 64. A portion of this condensate is returned to column 59 as reflux through a conduit 65. The remainder of the condensate is removed through a conduit 66. A side stream is removed from an upper region of column 59 through a conduit 67. This side stream comprises the benzene product.

The kettle product stream from fractionator 59 is passed through a conduit 68 to a fractionator column 59a. The kettle product from this column is passed by a conduit 68a to a fractionation column 59b. Fractionation columns 59a and 59b correspond generally to fractionation column 59, except that side cut product streams are not removed from these columns. The elements associated with columns 59a and 59b are designated by reference characters which correspond to those associated with column 59. A product stream comprising toluene is removed from accumulator 64a through a conduit 70. A product stream comprising xylenes is removed from accumulator 64b through a conduit 71. A product stream comprising heavy aromatics is removed from column 59b through a conduit 72.

A portion of the liquid solvent removed from the bottom of column 46 is passed by a conduit 77 to a storage vessel 78. Additional solvent can be added to vessel 78 as needed. The remainder of the solvent removed from column 46 is passed through a conduit 79 to a regenerator 80 which is provided with a reboiler 81.

Purified solvent is removed overhead and passed by a conduit 82 to storage vessel 78. A stream of sludge is removed through a conduit 83 and passed to a suitable disposal means. Purified solvent is removed from vessel 78 through conduit 31.

Figure 2:
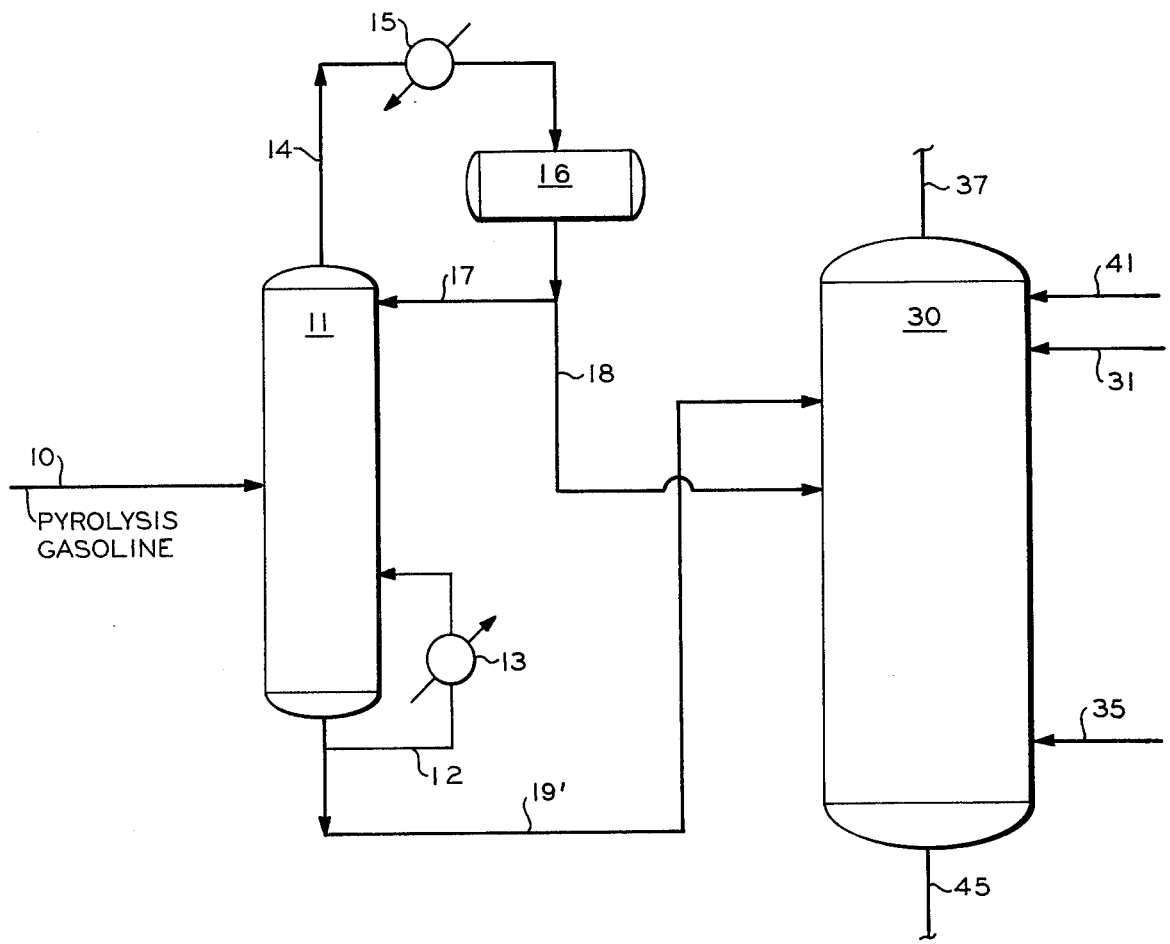
FIG. 2 illustrates apparatus which can be employed to carry out another method.

A second embodiment of this invention is illustrated in FIG. 2, wherein elements corresponding to those in FIG. 1 are designated by like reference numerals. In FIG. 2, fractionation column 20 is eliminated. The kettle product from column 11 is passed by conduit 19' to column 30 at an elevation above the point at which conduit 18 enters the column. In this embodiment, conduit 19' delivers a feed stream to conduit 30 which is rich in toluene and xylenes.

In a specific example of this invention, a pyrolysis gasoline is introduced into column 11 at a temperature of 156° C. and a pressure of 255 kPa. The columns of FIG. 1 are operated under the following conditions:

|  | Column No. | | | | | | |
|---|---|---|---|---|---|---|---|
|  | 11 | 20 | 30 | 46 | 59 | 59a | 59b |
| Top Temp. (° C) | 109 | 139 | 124 | 109 | 107 | 139 | 168 |
| Bottom Temp. (° C) | 166 | 186 | 169 | 177 | 164 | 188 | 213 |
| Top Pressure (kPa) | 241 | 207 | 241 | 172 | 207 | 207 | 207 |
| Bottom Pressure (kPa) | 279 | 248 | 276 | 200 | 262 | 241 | 266 |
| Number of Trays | 55 | 55 | 75 | 40 | 55 | 55 | 95 |

In order to simplify the drawing, various pumps, heaters, coolers and control valves to provide the foregoing conditions have been omitted. Suitable equipment of this type is well known in the art.

In this example wherein column 30 has 75 trays, conduits 29, 28 and 18 enter the column at tray Nos. 58, 42 and 30, respectively, measured from the bottom. The solvent, which is sulfolane containing about 2% by weight water, is introduced at tray No. 69. Reflux is introduced at the top tray. Under the foregoing conditions, the material balance has been calculated to be approximately as follows (expressed in lb. moles/day):

| Component | Conduit | | | | | | | | | |
|---|---|---|---|---|---|---|---|---|---|---|
|  | 10 | 18 | 19 | 28 | 29 | 31[(1)] | 45 | 42 | 43 | 47 |
| Cyclopentane | 181 | 181 |  |  |  |  |  | 181 |  |  |
| Normal hexane | 533 | 533 |  |  |  |  |  | 533 |  |  |
| Methylcyclopentane | 138 | 138 |  |  |  |  |  | 138 |  |  |
| Benzene | 6911 | 6898 | 13 | 13 |  |  | 6902 | 8 |  | 2 |
| Cyclohexane | 101 | 101 |  |  |  |  | 1 | 100 |  |  |
| Trimethylbutanes | 184 | 184 |  |  |  |  |  | 184 |  |  |
| Normal heptane | 234 | 210 | 23 | 23 |  |  |  | 234 |  |  |
| Methylcyclohexane | 167 | 17 | 150 | 150 |  |  | 7 | 160 |  |  |
| Tetramethylbutanes | 143 | 143 |  |  |  |  |  | 143 |  |  |
| Toluene | 3042 | 1 | 3041 | 3038 | 3 |  | 3029 | 13 |  |  |
| Normal octane | 189 |  | 189 | 167 | 22 |  | 2 | 187 |  |  |
| Ethylcyclohexane | 353 |  | 353 |  | 353 |  | 10 | 342 |  |  |
| Ethylbenzene | 272 |  | 272 |  | 272 |  | 269 | 3 |  |  |
| Para-xylene | 157 |  | 157 |  | 157 |  | 156 | 1 |  |  |
| Meta-xylene | 438 |  | 438 |  | 438 |  | 434 | 4 |  |  |
| Ortho-xylenes | 201 |  | 201 |  | 201 |  | 199 | 2 |  |  |
| Normal nonane | 244 |  | 244 |  | 244 |  | 20 | 224 |  |  |
| Cumene | 481 |  | 481 |  | 481 |  | 477 | 4 |  |  |
| Decane | 72 |  | 72 |  | 72 |  | 72 | 1 |  |  |
| $C_{10}$ aromatics | 613 |  | 613 |  | 613 |  | 608 | 5 |  |  |
| Water |  |  |  |  |  | 3042 |  |  | 3033 | 12789 |
| Sulfolane |  |  |  |  |  | 23054 | 23038 |  | 16 |  |

| Component | Conduit | | | | | | | | |
|---|---|---|---|---|---|---|---|---|---|
|  | 56 | 77 | 79 | 54 | 67[(2)] | 68 | 70 | 68a | 71 | 72 |
| Cyclopentane |  |  |  |  |  |  |  |  |  |  |
| Normal hexane |  |  |  |  |  |  |  |  |  |  |
| Methylcyclopentane |  |  |  |  |  |  |  |  |  |  |
| Benzene | 6902 |  |  | 2 | 6901 | 1 | 1 |  |  |  |
| Cyclohexane | 1 |  |  |  | 1 |  |  |  |  |  |
| Trimethylbutanes |  |  |  |  |  |  |  |  |  |  |
| Normal heptane |  |  |  |  |  |  |  |  |  |  |
| Methylcyclohexane | 7 |  |  |  | 4 | 3 | 3 |  |  |  |
| Tetramethylbutanes |  |  |  |  |  |  |  |  |  |  |
| Toluene | 3029 |  |  |  |  | 3029 | 3029 |  |  |  |

-continued

| | | | | | | |
|---|---|---|---|---|---|---|
| Normal octane | 2 | | | 2 | 2 | |
| Ethylcyclohexane | 10 | | | 10 | 10 | 10 |
| Ethylbenzene | 269 | | | 269 | 269 | 269 |
| Para-xylene | 156 | | | 156 | 156 | 156 |
| Meta-xylene | 434 | | | 434 | 434 | 434 |
| Ortho-xylenes | 199 | | | 199 | 199 | 199 |
| Normal nonane | 20 | | | 20 | 1 | 19 |
| Cumene | 477 | | | 477 | 1 | 476 |
| Decane | 71 | | | 71 | | 71 |
| $C_{10}$ aromatics | 607 | | | 607 | | 607 |
| Water | 268 | 3004 | 62 | 9455 | | |
| Sulfolane | | 22575 | 463 | | | |

[1] Total solvent to column 30, including 3300 lb. moles/day through conduit 32 and 5000 lb. moles/day through conduit 33.
[2] Approximately 5 lb. moles/day disposed through conduit 66.

While this invention has been described in conjunction with presently preferred embodiments, it obviously is not limited thereto.

What is claimed is:

1. A method of separating a pyrolysis gasoline which contains benzene, toluene, xylenes, paraffins and naphthenes, which method comprises:
    fractionating the pyrolysis gasoline to obtain a first stream rich in benzene, a second stream rich in toluene and a third stream rich in xylenes, the amounts of paraffins and naphthenes in said streams being determined by the boiling points of the paraffins and naphthenes;
    passing said first stream to an extractive distillation column at a first location intermediate the top and bottom thereof;
    passing said second stream to said extractive distillation column at a second location intermediate the top and bottom thereof, said second location being above said first location;
    passing said third stream to said extractive distillation column at a third location intermediate the top and bottom thereof, said third location being above said first and second locations;
    introducing into said extractive distillation column at a location above said third location a solvent which selectively absorbs aromatics in preference to paraffins and naphthenes;
    withdrawing a raffinate stream from said extractive distillation column, said raffinate stream containing a major portion of the paraffins and naphthenes present in said pyrolysis gasoline; and
    withdrawing an extract stream from said extractive distillation column, said extract stream containing a major portion of the benzene, toluene and xylenes present in said pyrolysis gasoline.

2. The method of claim 1 wherein said solvent sulfolane containing about 0.5 to 2.5 weight percent water.

3. The method of claim 1, further comprising removing solvent from said extract stream to obtain a fourth stream which contains benzene, toluene and xylenes, and fractionating said fourth stream to obtain fifth, sixth and seventh streams which are rich in benzene, toluene and xylenes, respectively.

4. The method of claim 3 wherein the solvent contains an aqueous phase which is recovered from said raffinate stream, said solvent is removed from said extract stream in a stripping column, and wherein the recovered aqueous phase of the solvent is introduced into the lower region of said stripping column.

5. The method of claim 1 wherein said raffinate stream is cooled to condense paraffins and naphthenes, and a portion of the resulting condensate is introduced into the upper region of said extractive distillation column as reflux.

6. A method of separating a fluid mixture of at least three constituents, wherein the first and second constituents are aromatic compounds which have different boiling points and can be separated from the third constituent selected from at least one of paraffins and naphthenes by extractive distillation using a solvent in which the first and second constituents are selectively absorbed in preference to the third constituent, the boiling point of the first constituent being lower than the boiling point of the second constituent, which method comprises:
    fractionating the fluid mixture to obtain a first stream rich in the first constituent and a second stream rich in the second constituent, the amounts of the third constituent in the first and second streams being determined by the boiling points of the three constituents;
    passing said first stream to an extractive distillation column at a first location intermediate the top and bottom thereof;
    passing said second stream to said extractive distillation column at a second location intermediate the top and bottom thereof, said second location being above said first location;
    introducing into said extractive distillation column at a location above said second location a solvent which selectively absorbs said first and second constituents in preference to said third constituent;
    withdrawing a raffinate stream from said extractive distillation column, said raffinate stream containing a major portion of said third constituent; and
    withdrawing an extract stream from said extractive distillation column, said extract stream containing a major portion of said first and second constituents.

7. The method of claim 6 wherein said fluid mixture includes benzene, toluene, xylenes, paraffins and naphthenes, said first stream is rich in benzene, said second stream is rich in toluene and xylenes, said raffinate stream contains a major portion of said paraffins and naphthenes and said extract stream contains a major portion of said benzene, toluene and xylenes.

8. The method of claim 7 wherein said solvent is sulfolane containing about 0.5 to 2.5 weight percent water.

9. The method of claim 6 wherein the fluid mixture contains a fourth constituent having a boiling point intermediate the boiling points of the first and second constituents, said fourth constituent also being selectively absorbed by said solvent in preference to said third constituent, and comprising further fractionating said fluid mixture to obtain a third stream rich in said fourth constituent, and passing said third stream to said extractive distillation column at a third location intermediate said first and second locations.

* * * * *